United States Patent
Li et al.

(10) Patent No.: US 10,688,563 B2
(45) Date of Patent: Jun. 23, 2020

(54) MANUFACTURING METHOD OF MULTILAYER SHELL-CORE COMPOSITE STRUCTURAL COMPONENT

(71) Applicants: Yadong Li, Suzhou (CN); Yajun Li, Suzhou (CN)

(72) Inventors: Yadong Li, Suzhou (CN); Yajun Li, Suzhou (CN)

( * ) Notice: Subject to any disclaimer, the term of this patent is extended or adjusted under 35 U.S.C. 154(b) by 254 days.

(21) Appl. No.: 15/886,836

(22) Filed: Feb. 2, 2018

(65) Prior Publication Data
US 2018/0154447 A1 Jun. 7, 2018

Related U.S. Application Data

(62) Division of application No. 14/938,846, filed on Nov. 12, 2015, now Pat. No. 9,937,559, which is a division
(Continued)

(30) Foreign Application Priority Data

Oct. 8, 2010 (CN) .......................... 2010 1 0299138

(51) Int. Cl.
*B22F 7/02* (2006.01)
*B22F 3/15* (2006.01)
(Continued)

(52) U.S. Cl.
CPC .................. *B22F 7/02* (2013.01); *A61F 2/32* (2013.01); *A61F 2/34* (2013.01); *A61F 2/3601* (2013.01);
(Continued)

(58) Field of Classification Search
CPC ..... A61F 2/34; C04B 2335/6022; B22F 3/225
See application file for complete search history.

(56) References Cited

U.S. PATENT DOCUMENTS 6,241,773 B1 * 6/2001 Tashima ................ A61L 27/105
623/23.56
2002/0010070 A1 * 1/2002 Cales ........................ A61F 2/32
501/105
(Continued)

FOREIGN PATENT DOCUMENTS

WO    WO-2011016718 A1 * 2/2011 ....... C04B 35/63488

*Primary Examiner* — Erin Snelting
(74) *Attorney, Agent, or Firm* — Kilpatrick Townsend & Stockton, LLP (57) ABSTRACT

A manufacturing method of a multilayer shell-core composite structural component comprises the following procedures: (1) respectively preparing feeding material for injection forming of a core layer, a buffer layer and a shell layer, wherein the powders of feeding material of the core layer and the shell layer are selected from one or more of metallic powder, ceramic powder or toughened ceramic powder, and are different from each other, and the powder of feeding material of the buffer layer is gradient composite material powder; (2) layer by layer producing the blank of multilayer shell-core composite structural component by powder injection molding; (3) degreasing the blank; and (4) sintering the blank to obtain the multilayer shell-core composite structural component. The multilayer shell-core composite structural component has the advantages of high surface hardness, abrasion resistance, uniform thickness of the shell layer, stable and persistent performance.

16 Claims, 5 Drawing Sheets

Related U.S. Application Data of application No. 13/878,233, filed as application No. PCT/CN2011/076586 on Jun. 29, 2011, now Pat. No. 9,216,454.

(51) Int. Cl.

| | | |
|---|---|---|
| *C04B 35/634* | (2006.01) | |
| *C04B 35/638* | (2006.01) | |
| *C04B 35/645* | (2006.01) | |
| *A61F 2/34* | (2006.01) | |
| *C04B 35/64* | (2006.01) | |
| *B22F 3/10* | (2006.01) | |
| *B22F 3/105* | (2006.01) | |
| *B22F 3/22* | (2006.01) | |
| *B22F 7/06* | (2006.01) | |
| *B32B 18/00* | (2006.01) | |
| *C04B 35/111* | (2006.01) | |
| *C04B 35/119* | (2006.01) | |
| *C04B 35/488* | (2006.01) | |
| *A61F 2/32* | (2006.01) | |
| *B22F 3/12* | (2006.01) | |
| *B22F 7/00* | (2006.01) | |
| *A61F 2/36* | (2006.01) | |

(52) U.S. Cl.
CPC ............ *B22F 3/105* (2013.01); *B22F 3/1021* (2013.01); *B22F 3/12* (2013.01); *B22F 3/15* (2013.01); *B22F 3/225* (2013.01); *B22F 7/008* (2013.01); *B22F 7/06* (2013.01); *B32B 18/00* (2013.01); *C04B 35/111* (2013.01); *C04B 35/119* (2013.01); *C04B 35/4885* (2013.01); *C04B 35/634* (2013.01); *C04B 35/638* (2013.01); *C04B 35/64* (2013.01); *C04B 35/6455* (2013.01); *C04B 2235/3225* (2013.01); *C04B 2235/3229* (2013.01); *C04B 2235/6022* (2013.01); *C04B 2235/77* (2013.01); *C04B 2235/96* (2013.01); *C04B 2237/343* (2013.01); *C04B 2237/348* (2013.01); *C04B 2237/58* (2013.01); *C04B 2237/84* (2013.01)

(56) References Cited

U.S. PATENT DOCUMENTS

| | | | | |
|---|---|---|---|---|
| 2002/0031675 | A1* | 3/2002 | Cales | A61F 2/32 428/472 |
| 2008/0145672 | A1* | 6/2008 | Willkens | B28B 1/008 428/426 |
| 2008/0199343 | A1* | 8/2008 | Rust | A61F 2/34 419/6 |
| 2009/0129961 | A1* | 5/2009 | Lavoie | B22F 3/225 419/10 |
| 2009/0187255 | A1* | 7/2009 | Jani | A61L 27/306 623/23.53 |
| 2012/0235330 | A1* | 9/2012 | ter Maat | B22F 3/1021 264/645 |

\* cited by examiner

MANUFACTURING METHOD OF MULTILAYER SHELL-CORE COMPOSITE STRUCTURAL COMPONENT

CROSS REFERENCE TO RELATED APPLICATIONS

The present application is a divisional application of U.S. application Ser. No. 14/938,846, filed on Nov. 12, 2015 which is a divisional application of U.S. application Ser. No. 13/878,233, filed on Apr. 8, 2013 which is a national stage application of PCT/CN2011/076586, filed on Jun. 29, 2011 which claims the priority of Chinese Patent Application No. 201010299138.8, filed on Oct. 8, 2010, the entire disclosures of which are incorporated herein by reference.

TECHNICAL FIELD

The present disclosure generally relates to manufacturing a multilayer shell-core structural component, and more particularly, to a multilayer shell-core composite structural component with a spherical, hemispheric, hemispherical shell, columnar, tubular, or irregular shape.

BACKGROUND

Components with a spherical, hemispheric, hemispherical shell, columnar or tubular shape, or any other irregular shape are widely used in all kinds of fields. In most applications, the components are not only required to have good properties of wear-resistance, corrosion-resistance and heat-resistance, high-precision of dimensional coordination and smooth finished surface, but also have high toughness, mechanical bearing capacity, and machinability. The common components may include an artificial femoral ball head in total hip arthroplasty components, an artificial acetabulum with a hemispherical shell shape, a plunger with a columnar shape, a ball valve body with a tubular shape, and an irregular femoral condyle prosthesis, i.e. prosthetic knees, and so on.

Ceramic material has characteristics of high surface hardness, wear-resistance, and corrosion-resistance. However, it has low flexural strength and low fracture toughness with bad mechanical bearing capacity. Components made of ceramic material are more likely to crack brittlely, therefore can not be used to manufacture the above mentioned components individually. In the existing techniques, composite toughened ceramic emerges to improve fracture toughness of the common ceramic. However, composite toughened ceramic, despite its high fracture toughness, has some drawbacks compared with the common ceramic. For example, alumina ceramic with introduction of zirconium dioxide ($ZrO_2$) has its surface hardness and compression resistance strength to be lowered. Ceramic with introduction of whisker or fiber has its density and wear-resistance property to be decreased.

To solve above problems, there appears, in the existing techniques, a shell-core structural component which includes a shell layer of ceramic and a core layer of metal, by forming a ceramic film on the surface of a metal using all kinds of physical or chemical methods, so as to increase wear resistance, corrosion resistance and heat resistance of the component. The shell-core structural component has a metal core, and it has excellent flexural strength, and high fracture toughness and machinability, which thereby is not likely to crack. In addition, the shell-core structural component has a ceramic shell, it has high surface hardness, and good wear resistance, corrosion resistance and heat resistance. That is, the shell-core structural component combines advantages of both metal and ceramic. Usually, the above-mentioned ceramic film is formed using a physical or chemical deposition. However, the ceramic film formed by these methods are thin in thickness, ranging from several micrometers to tens of micrometers, weak in adhesive strength between the shell layer and the core layer, poor in mechanical bearing capacity, and poor in durability and stability of wear-resistance and corrosion-resistance.

In order to increase the thickness of the ceramic shell layer and adhesive strength between the shell layer and the core layer, there provides three methods in the existing technology and will be described below. The first method may include: mixing ceramic powder, metal powder, and compound powder having different proportions of ceramic powder and metal powder, with organic carrier to obtain a slurry with a certain solid loading; tape casting, stacking and cold pressing to form a green body of a multilayer shell-core composite structural component having a shell layer, a transition layer, and a core layer; and sintering the green body to obtain a multilayer shell-core composite structural component. The second method may include: dry powder cold pressing repeatedly on ceramic powder, metal powder and compound powder having different proportions of ceramic powder and metal powder, to form a green body of a multilayer shell-core composite structural component having a shell layer, a transition layer and a core layer; and sintering the green body to obtain a multilayer shell-core composite structural component. The third method may include: mixing ceramic powder, metal powder and compound powder having different proportions of ceramic powder and metal powder with a solvent like deionized water to obtain a suspension liquid with a certain solid loading; electrostatic depositing on the suspension liquid in multiple steps to obtain a green body of a multilayer shell-core composite structural component having a shell layer, a transition layer and a core layer; and sintering the green body to obtain a multilayer shell-core composite structural component. However, the above mentioned methods have following disadvantages, such as hard to form an irregular shape, layers in high and even thickness, and hard to accurately control the thickness of each layer, and microstructure and performance of the multilayer shell-core composite structural component. Thus, it is difficult to apply the existing methods to form a multilayer shell-core composite structural component required in this disclosure. That is, using the existing methods, it is difficult to obtain a multilayer shell-core composite structural component having high surface hardness, high wear resistance, corrosion resistance and heat resistance, high adhesive strength between the shell layer and the core layer, good mechanical bearing capacity, high fracture toughness, and high matching ability and stability of performance.

SUMMARY

The present disclosure provides a method for manufacturing a multilayer shell-core composite structural component, realizing a formation of precision components with a spherical, hemispheric, hemispherical-shell, columnar, or tubular shape, or an irregular shape in a multilayer shell-core composite structural component, and improving adhesive strength between the shell layer and the core layer, wear resistance, corrosion resistance, heat resistance of the shell layer, and toughness and resistance to breakage of the core layer.

Embodiments of the present disclosure provide a method for manufacturing a multilayer shell-core composite structural component. The method includes:

(1) preparing feedstocks of a shell layer, a transition layer and a core layer for powder injection molding, respectively, the feedstocks being obtained by mixing a powder, an binder and an additive including a surface active agent and a plasticizer; where the powder of the feedstock of the core layer may be selected from one or more of a metal powder, a ceramic powder and a toughened ceramic powder; the powder of the feedstock of the shell layer may be selected from one or more of a metal powder, a ceramic powder and a toughened ceramic powder; the powder of the feedstock of the core layer is different from the powder of the feedstock of the shell layer, and the powder of the feedstock of the transition layer is a powder of gradient composite material;

(2) performing a powder injection molding using the prepared feedstocks in step (1), to obtain a green body of the multilayer shell-core composite structural component including the shell layer, the transition layer and the core layer;

(3) performing debinding on the green body obtained in step (2); and (4) sintering the green body after being debound in step (3), to obtain the multilayer shell-core composite structural component based on properties of the materials used in the shell layer, the transition layer and the core layer.

In some embodiments, the material of the transition layer may be selected depending on thermal expansion coefficients of the shell layer and the core layer, and negative chemical reaction degree between the shell layer and the core layer, so that situations of a reduction of stress mismatch of the interlayer interface, and a degradation of interlayer adhesive strength and even crack, which are caused by different thermal expansion coefficients of the shell layer and the core layer, may be relieved and chemical reaction between the shell layer and the core layer when they are in direct contact under certain conditions (e.g., in elevated temperature sintering) may be avoided. Appropriate materials for the transition layer may be selected according to actual requirements. The transition layer may have a thickness ranging from about 0.1 mm to about 20 mm. The additive may include a surface active agent and a plasticizer as needed. In some embodiments, after the green body of the component is obtained in step (2), a surface finishing may be performed on the green body to ensure the product's quality. After being sintered, micro-machining and surface polishing may be performed on the component, for example, using SiC ultrafine powder and diamond abrasive paste to micromachine and polish the ceramic surface, to obtain a multilayer shell-core composite structural component having a smooth finished surface and a proper dimensional coordination. The binder may include thermoplastic binder, thermosetting binder, gel binder and polymer binder. The debinding process in step (3) may include catalytic debinding, heating debinding, dissolution extraction debinding, supercritical fluid extraction (SFE) debinding or siphon debinding. The sintering process in step (4) may include high-temperature atmospheric-pressure sintering, vacuum sintering, controlled atmosphere sintering, hot pressed sintering, or Hot Isostatic Pressing sintering, in a reducing atmosphere or an inert atmosphere, such as in atmosphere, nitrogen, argon, vacuum or hydrogen.

In some embodiments, the powder injection molding may be performed in two different ways. For example, in step (2): performing injection moldings in multiple steps on an ordinary powder injection molding machine, using multiple sets of moulds successively, to obtain a green body of the composite structural component including the shell layer, the transition layer and the core layer.

Alternatively, in step (2): performing a co-injection molding through an injection device driven by a slider block on a multi-material powder co-injection machine to obtain a green body of the composite structural component including the shell layer, the transition layer and the core layer.

The transition layer may have a single-layer or multi-layer structure. For a multi-layer transition layer, feedstock of each layer of the transition layer may be prepared respectively, and the transition layer may be formed layer by layer through powder injection molding.

The ceramic powder may be one or more selected from a group consisting of alumina, zirconia, titanium carbide, chromium carbide, silicon carbide, boron carbide, zirconium carbide, tantalum carbide, tungsten carbide, titanium nitride, chromium nitride, boron nitride, silicon nitride, zirconium nitride and tantalum nitride. The metal powder may be one or more selected from a group consisting of niobium, zirconium, titanium, molybdenum, tantalum, cobalt, chromium, vanadium, aluminum and iron. Generally, the core layer may be made of metal powder, and the shell layer may be made of ceramic powder. Alternatively, the shell layer may be made of ceramic powder, and the core layer may be made of another kind of ceramic powder or toughened ceramic powder. Or, the shell layer may be made of metal powder, and the core layer may be made of ceramic powder or toughened ceramic powder. The transition layer may ensure a strong adhesive strength between the shell layer and the core layer.

The toughened ceramic may be metal-based or ceramic-based cermet which may be composed of a ceramic or a metal described above, or ceramic toughened by zirconia, whisker or fiber. Specifically, the toughened ceramic may include:

(1) cermet: (a) oxide-based cermet, which may be obtained by using alumina or zirconia as a base, composited with a metal such as niobium, titanium, zirconium, molybdenum, tantalum, cobalt, Chromium, vanadium, aluminum or iron. (b) carbide-based cermet, which may be obtained by using titanium carbide, chromium carbide, silicon carbide, boron carbide, zirconium carbide, tantalum carbide or tungsten carbide as a base, composited with a metal such as niobium, titanium, zirconium, molybdenum, tantalum, cobalt, chromium, vanadium, aluminum or iron. (c) nitride-based cermet, which may be obtained by using titanium nitride, chromium nitride, boron nitride, silicon nitride, zirconium nitride or tantalum nitride as a base, composited with a metal such as niobium, titanium, zirconium, molybdenum, tantalum, cobalt, chromium, vanadium, aluminum or iron. (d) metal-based cermet, which may be obtained by using a metal such as niobium, titanium, zirconium, molybdenum, tantalum, cobalt, chromium, vanadium, aluminum or iron as a base, composited with oxide powder or non-oxide powder.

(2) $ZrO_2$ toughened ceramic, which may be MgO, $CeO_2$ or $Y_2O_3$ partially stabilized $ZrO_2$ toughened ceramic, or may be used as a toughening additive. The $ZrO_2$ toughened ceramic may be spread uniformly in oxide powder or non-oxide powder, then being calcined to obtain $ZrO_2$ toughened composite oxide ceramic or composite non-oxide ceramic having an excellent sintering activity.

(3) whisker or fiber toughened ceramic, which may be composited using whisker like SiC or $Si_3N_4$ whisker, or short-staple like carbon fiber or SiC short-staple, with a ceramic such as alumina, zirconia, titanium carbide, chromium carbide, silicon carbide, boron carbide, zirconium carbide, tantalum carbide, tungsten carbide, titanium nitride, chromium nitride, boron nitride, silicon nitride, zirconium nitride or tantalum nitride.

The powder of gradient composite material of the feedstock of the transition layer may be formed by mixing a powder of the feedstock of the shell layer with a powder of the feedstock of the core layer. The mixing ratio varies progressively in gradient, with the powder of the feedstock of the shell layer taking up a main proportion close to the shell, while the powder of the feedstock of the core layer taking up a main proportion close to the core. The transition layer may be formed layer by layer using multiple injection molding steps. The gradient composite layer may relieve thermal expansion coefficients mismatch (heat stress) between the shell layer and the core layer, prevent negative chemical reaction, and transitionally match the shell layer and the core layer in chemical or physical characteristics.

Generally, the shell layer or the core layer may have a thickness ranging from about 0.1 mm to about 20 mm. The transition layer may have a thickness ranging from about 0.1 mm to about 20 mm. Each layer may have a relative density of more than 97%.

The multilayer shell-core composite structural component may be spherical, hemispheric, hemispherical-shell, columnar or tubular, or other irregularly shaped.

By using the above technical solutions, (1) a ceramic shell layer may be obtained with a thickness ranging from about 0.1 mm to about 20 mm. The ceramic shell layer may has a high shell surface hardness (HV>1300), and high wear resistance, corrosion resistance and high surface finish; (2) a toughened core layer may be obtained having properties of high flexural strength, high load capacity and high fracture toughness ($K_{IC}$>8 MPa·m$^{1/2}$); and (3) a transition layer may be formed between the ceramic shell layer and the toughened core layer to decrease interface stress and prevent negative chemical reaction, based on a match degree of the microstructures and properties, and possibility of negative chemical reaction. (4) The ceramic shell layer and the toughened core formed by high-temperature sintering have advantages of high interlayer adhesive strength, good mechanical bearing capacity, and high matching ability and stability of performance.

Compared with the conventional technology, this disclosure has the following advantages:

1. By using multi-material powder co-injection molding, a multilayer shell-core composite structural component is obtained. In the conventional technology, the powder injection molding method can only be used to form a ceramic component in a single material or a metal component in a single material. There is no any report about manufacturing a ceramic and metal multilayer shell-core composite structural component. The present disclosure proposes a concept of a ceramic and metal multi-material powder co-injection molding process, and achieves a multilayer shell-core composite structural component using the processes.

2. By using multi-material powder co-injection molding, a transition layer is formed between the shell layer and the core layer. Thus the defects of a mismatch of the microstructures and properties, high possibility of negative chemical reactions, and low adhesive strength, caused by the differences of chemical or physical properties between the shell layer and the core layer, can be overcome. The problems that a component with a spherical, hemispheric, hemispherical-shell, columnar, or tubular shape, or irregular shape can not be manufactured, thickness of each layer can not be accurately controlled, and a microstructure and performance of each layer can not be accurately controlled by the existing dry powder cold pressing molding, tape casting, or electrostatic deposition processes, can be overcome.

3. The multilayer shell-core structural component of the present disclosure, has a ceramic shell layer with a high hardness in the shell surface, high wear resistance, corrosion resistance, and heat resistance, and high matching ability and stability of performances. The shell layer is large and homogeneous in thickness and has a dense microstructure. The shell layer is combined with the core layer through a transition layer, so the multilayer shell-core structural component has high adhesive strength, high flexural strength, high fracture toughness and crack resistance, excellent mechanical bearing capacity, and high matching ability and stability of performance.

4. The multi-material powder co-injection molding processes according to the present disclosure are simple to implement, high precise in size control, near net shape in forming processes, and have high production efficiency and low cost, which is more adaptable for manufacturing components with irregular shape.

DETAILED DESCRIPTION

Hereinafter, the disclosure will be described in detail with several embodiments in conjunction with the accompanying drawings.

First Embodiment

A femoral ball head having a multilayer shell-core composite structure, is composed of a ceramic spherical shell layer 1 including high purity and superfine alumina, an alumina-based (niobium) cermet interlayer 5 (namely, transition layer), and a niobium metal core 2. The multilayer composite structure may have five different structures, which are illustrated in FIG. 1 to FIG. 5 and may be selected according to requirements of practical applications.

Figure 1:
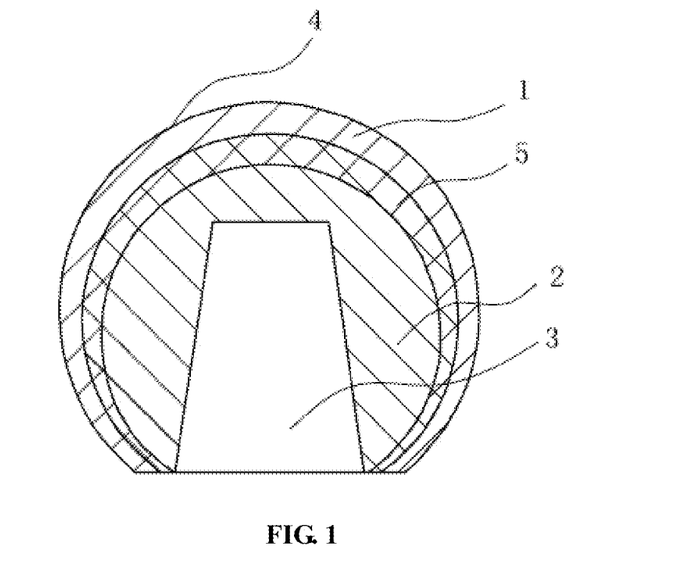
FIG. 1 to FIG. 5 schematically illustrate several different cross-sectional views of artificial femoral ball heads having a multilayer shell-core composite structure according to a first and second embodiments of the present disclosure.
Figure 2:
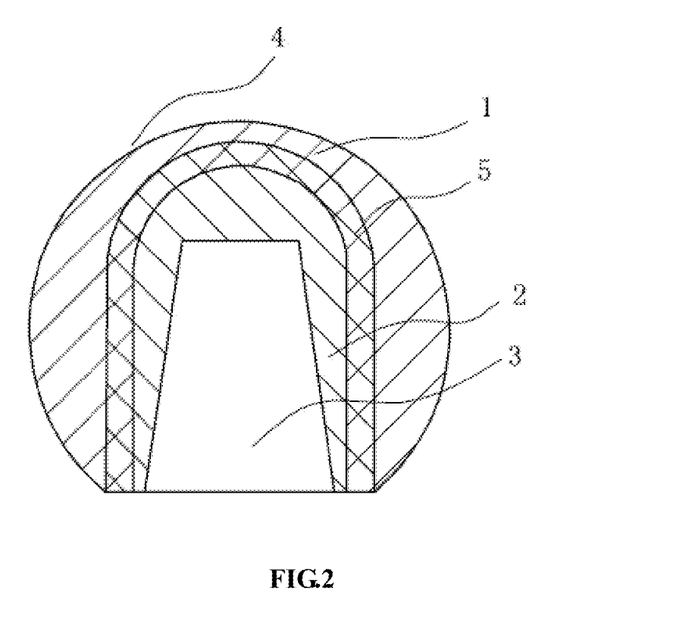
Figure 3:
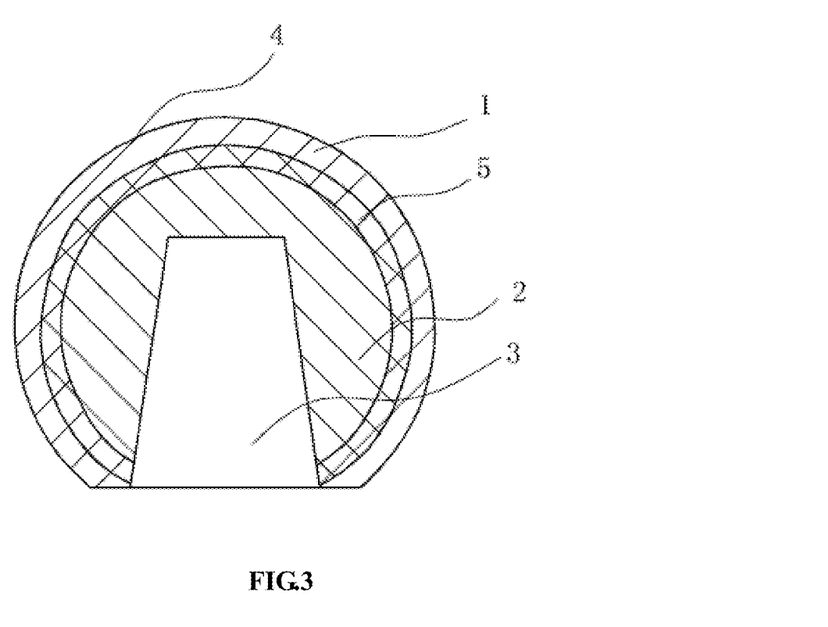
Figure 4:
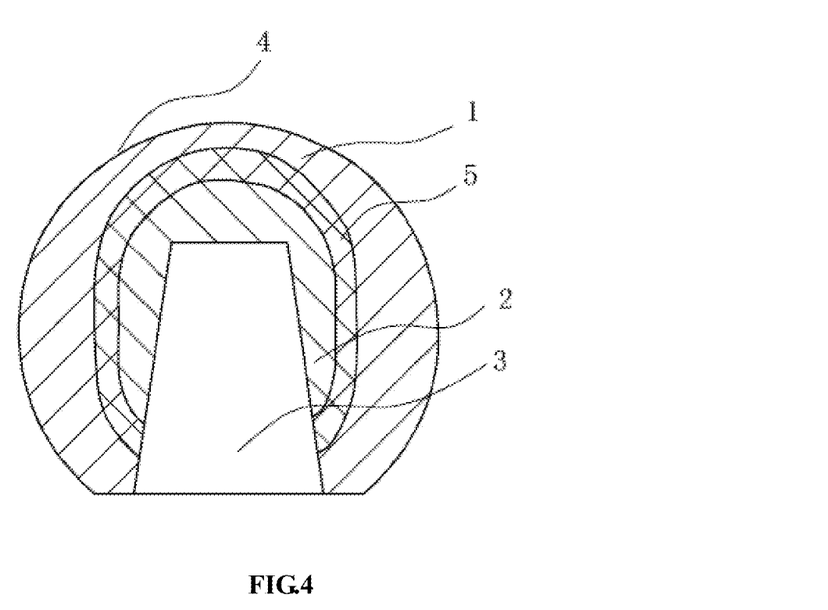
Figure 5:
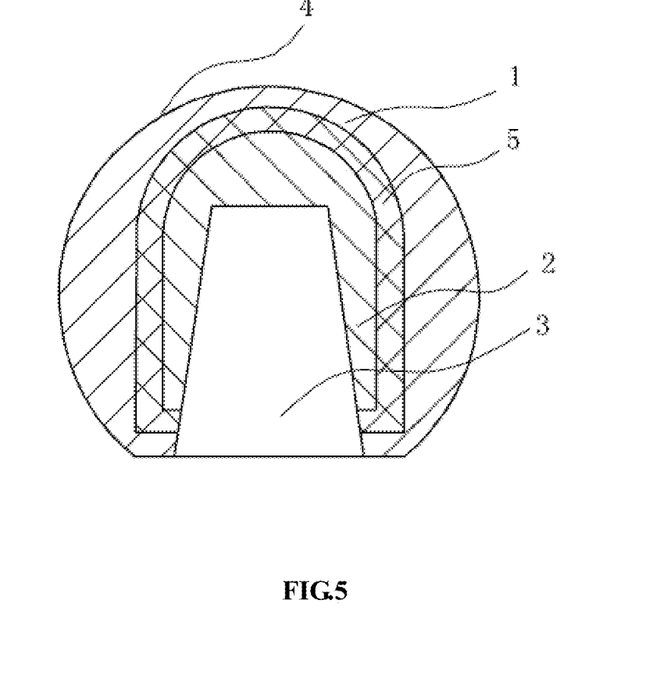
Figure 6:
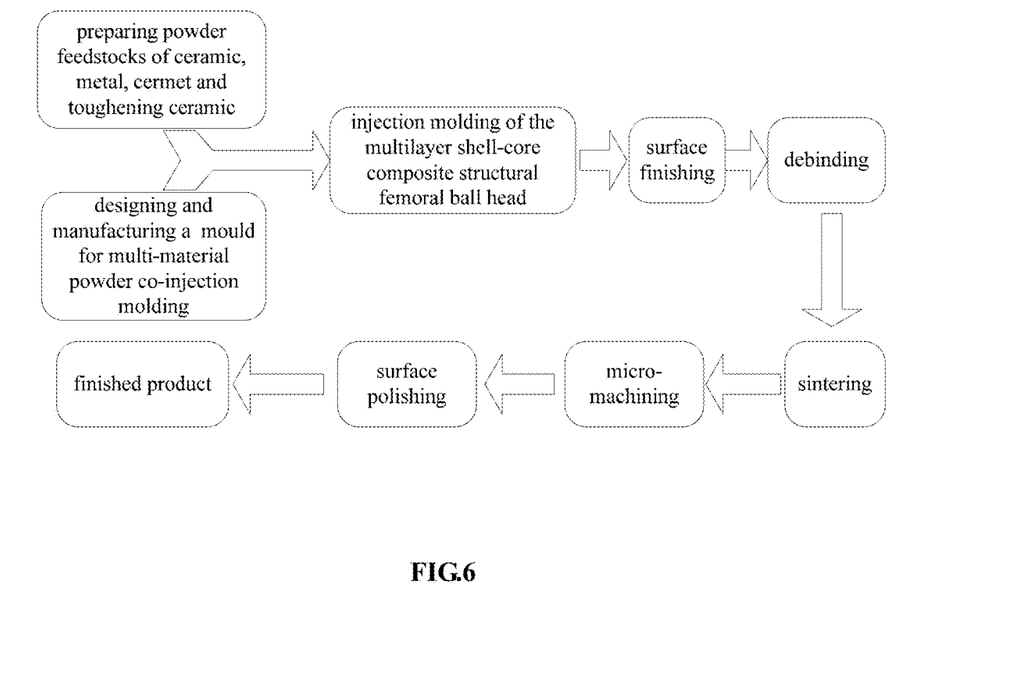
FIG. 6 is schematically illustrates a flow chart of a manufacturing method of a multilayer shell-core structural component according to an embodiment of the present disclosure.

Referring to FIG. 6, a method for manufacturing a femoral ball head having a multilayer shell-core composite structure in the first embodiment may include:

(1) preparing feedstocks for powder injection molding which include high-purity and superfine alumina powder, alumina-based (niobium) cermet compound powder, and niobium metal powder. The high-purity and superfine alumina powder may have a purity greater than 99.9 wt %, have a particle size ranging from 0.5 μm to 10 μm. The niobium metal powder may have a purity greater than 99.8 wt %, have a particle size ranging from 0.5 μm to 10 μm. In order to decrease sintering temperature and improve sintering performance, magnesium oxide (MgO) powder with a concentration of 0.25 wt. % may be added into the high-purity and superfine alumina powder, and cobalt (Co) powder with a concentration of 3 wt. % may be added into the niobium metal powder, both of which may act as sintering aids. After preparation, the modified alumina powder, alumina-based (niobium) cermet compound powder and niobium metal powder are mixed with polyoxymethylene resin binder (89 wt. % polyformaldehyde, 5 wt. % high density polyethylene and 6 wt. % other binding assistant agent), respectively. The mixture is then mixed under a temperature of about 180° C. for about two and a half hours, so that a feedstock called as polyaldehydes system is obtained, which has a solid loading (solid content) greater than 55 vol. %.

(2) by using three sets of moulds, performing injection molding successively to obtain the niobium metal core 2, the alumina-based (niobium) cermet interlayer 5, and the alumina spherical shell layer 1, of the femoral ball head having a multilayer shell-core composite structure including alumina ceramic—alumina-based (niobium) cermet interlayer—niobium metal. Firstly, feedstocks including niobium metal polyaldehydes are injected into a core mould (a first mould) to obtain the niobium metal core 2 having a bore-hole 3. Then, by using the niobium metal core 2 as an insert, a complex with the alumina-based (niobium) cermet interlayer 5 covering the niobium metal core 2 may be obtained through injection molding in a second mould. Then, by using the complex with the alumina-based (niobium) cermet interlayer 5 covering the niobium metal core 2 as an insert, a green body of the femoral ball head having a multilayer shell-core composite structure, which includes alumina ceramic—alumina-based (niobium) cermet interlayer—niobium metal, may be obtained through injection molding in a third mould. The temperature of the injection may be in a range from about 170° C. to about 180° C., the pressure of the injection may be in a range from about 110 MPa to about 130 MPa, the dwell pressure may be in a range from about 70 MPa to about 80 MPa, and the cooling time may be in a range from about 3 minutes to about 4 minutes.

(3) if necessary, performing surface finishing on an alumina spherical shell surface 4 and the bore-hole 3 formed in the niobium metal core 2 of the green body of the femoral ball head having a multilayer shell-core composite structure, which includes alumina ceramic—alumina-based (niobium) cermet interlayer—niobium metal.

(4) performing catalytic debinding on the green body of the femoral ball head having a multilayer shell-core composite structure including alumina ceramic—alumina-based (niobium) cermet interlayer—niobium metal in an atmosphere furnace with a temperature ranging from about 110° C. to about 120° C., where hydrogen nitrate is used as debinding catalyst, nitrogen is used as debinding carrier gas, and the catalytic debinding process may last for about 5 hours.

(5) after being catalytic debound, sintering the green body of the femoral ball head having a multilayer shell-core composite structure including alumina ceramic—alumina (niobium) transition layer—niobium metal in a controlled atmosphere Hot Isostatic Pressing (HIP) furnace, where the sintering is performed at a temperature of about 1450° C., a pressure of about 35 MPa, and the soaking time is about 1 hour, so that an alumina spherical shell layer 1 which has a relative density greater than 99% and a hardness greater than HV1950, an alumina (niobium) transition layer 5 which becomes densification and toughness and the niobium metal core 2, may be obtained.

(6) according to size requirements of the products, performing micro-machining on the alumina ceramic spherical shell surface 4 and the bore-hole 3 of the sintering body of the femoral ball head having a multilayer shell-core composite structure, which includes alumina ceramic—alumina-based (niobium) cermet interlayer—niobium metal.

(7) finally, polishing the alumina ceramic spherical shell surface 4 by using SiC ultrafine powder and diamond abrasive paste, to obtain the femoral ball head having a multilayer shell-core composite structure including alumina ceramic-alumina-based (niobium) cermet interlayer—niobium metal, so that a smooth finished surface, and a proper dimensional coordination between the bore-hole 3 and the femoral component may be obtained.

Second Embodiment

A femoral ball head having a multilayer shell-core composite structure, includes a ceramic spherical shell layer 1 including high purity and superfine alumina, a toughened ceramic interlayer 5 of $ZrO_2(3Y_2O_3)$-80 wt. % $Al_2O_3$ and a toughened ceramic core 2 of $ZrO_2(3Y_2O_3)$-20 wt. % $Al_2O_3$.

Referring to FIG. 6, a method for manufacturing a femoral ball head having a multilayer shell-core composite structure in the second embodiment may include:

(1) preparing feedstocks for powder injection molding which include high-purity and superfine alumina powder, and compound powder of $ZrO_2(3Y_2O_3)$-80 wt. % $Al_2O_3$ and compound powder of $ZrO_2(3Y_2O_3)$-20 wt. % $Al_2O_3$. The high-purity and superfine alumina powder may have a purity greater than 99.9 wt %, and a particle size ranging from 0.5 μm to 10 μm. The $ZrO_2$ powder may have a purity greater than 99.8 wt %, and a particle size ranging from 0.5 μm to 10 μm. In order to decrease sintering temperature and improve sintering performance, magnesium oxide (MgO) powder with a concentration of 0.25 wt. % may be added into the high-purity and superfine alumina powder as sintering aids. After preparation, the modified alumina powder, compound powder of $ZrO_2(3Y_2O_3)$-80 wt. % $Al_2O_3$ and compound powder of $ZrO_2(3Y_2O_3)$-20 wt. % $Al_2O_3$ are mixed with polyoxymethylene resin binder (89 wt. % polyformaldehyde, 5 wt. % high density polyethylene and 6 wt. % other binding assistant agent), respectively. The mixture is then mixed under a temperature of about 180° C. for about two and a half hours, so that a feedstock of polyaldehydes system, having a solid loading (solid content) greater than 55 vol. %, can be obtained.

(2) by using three sets of moulds, performing injection molding successively to obtain the core 2 of $ZrO_2(3Y_2O_3)$-20 wt. % $Al_2O_3$, the interlayer 5 of $ZrO_2(3Y_2O_3)$-80 wt. % $Al_2O_3$, and the alumina spherical shell layer 1 of the femoral ball head having a multilayer shell-core composite structure including alumina ceramic—interlayer of $ZrO_2(3Y_2O_3)$-80 wt. % $Al_2O_3$—core of $ZrO_2(3Y_2O_3)$-20 wt. % $Al_2O_3$. Firstly, feedstocks including $ZrO_2(3Y_2O_3)$-20 wt. % $Al_2O_3$ polyaldehydes are injected into a core mould (a first mould) to obtain the core 2 of $ZrO_2(3Y_2O_3)$-20 wt. % $Al_2O_3$ having a bore-hole 3. Then, by using the core 2 of $ZrO_2(3Y_2O_3)$-20 wt. % $Al_2O_3$ as an insert, a complex with the interlayer 5 of $ZrO_2(3Y_2O_3)$-80 wt. % $Al_2O_3$ covering the core 2 of $ZrO_2(3Y_2O_3)$-20 wt. % $Al_2O_3$ may be obtained through injection molding in a second mould. Then, using the complex with the interlayer 5 of $ZrO_2(3Y_2O_3)$-80 wt. % $Al_2O_3$ covering the core 2 of $ZrO_2(3Y_2O_3)$-20 wt. % $Al_2O_3$ as an insert, a green body of the femoral ball head having a multilayer shell-core composite structure including alumina ceramic—interlayer of $ZrO_2(3Y_2O_3)$-80 wt. % $Al_2O_3$—core of $ZrO_2(3Y_2O_3)$-20 wt. % $Al_2O_3$, may be obtained through injection molding in a third mould. The temperature of the injection may be in a range from about 170° C. to about 180° C., the pressure of the injection may be in a range from about 110 MPa to about 130 MPa, the dwell pressure may be in a range from about 70 MPa to about 80 MPa, and the cooling time may be in a range from about 3 minutes to about 4 minutes.

(3) if necessary, performing surface finishing on an alumina spherical shell surface 4 and the bore-hole 3 formed in the core 2 of $ZrO_2(3Y_2O_3)$-20 wt. % $Al_2O_3$ of the green body of the femoral ball head having a multilayer shell-core composite structure including alumina ceramic—interlayer of $ZrO_2(3Y_2O_3)$-80 wt. % $Al_2O_3$—core of $ZrO_2(3Y_2O_3)$-20 wt. % $Al_2O_3$.

(4) performing catalytic debinding on the green body of the femoral ball head having a multilayer shell-core composite structure including alumina ceramic—interlayer of $ZrO_2(3Y_2O_3)$-80 wt. % $Al_2O_3$—core of $ZrO_2(3Y_2O_3)$-20 wt. % $Al_2O_3$ in an atmosphere furnace with a temperature ranging from about 110° C. to about 120° C., where hydrogen nitrate is used as debinding catalyst, nitrogen is used as debinding carrier gas, and the catalytic debinding may last for about 5 hours.

(5) after being catalytic debound, sintering the green body of the femoral ball head having a multilayer shell-core composite structure including alumina ceramic—interlayer of $ZrO_2(3Y_2O_3)$-80 wt. % $Al_2O_3$—core of $ZrO_2(3Y_2O_3)$-20 wt. % $Al_2O_3$ in an air furnace, where the sintering may be performed at a temperature of about 1600° C., and the soaking time is about 1 hour, so that an alumina spherical shell layer 1 which has a relative density greater than 99%, a hardness greater than HV1950, an interlayer 5 of $ZrO_2(3Y_2O_3)$-80 wt. % $Al_2O_3$ which is densified and toughed and a core 2 of $ZrO_2(3Y_2O_3)$-20 wt. % $Al_2O_3$ which has a fracture toughness greater than 10 $MPa \cdot m^{1/2}$, may be obtained.

(6) according to size requirements of the products, performing micro-machining on the alumina ceramic spherical shell surface 4 and the bore-hole 3 of the sintering body of the femoral ball head having a multilayer shell-core composite structure including alumina ceramic—interlayer of $ZrO_2(3Y_2O_3)$-80 wt. % $Al_2O_3$—core of $ZrO_2(3Y_2O_3)$-20 wt. % $Al_2O_3$.

(7) finally, polishing the alumina ceramic spherical shell surface 4 by using SiC ultrafine powder and diamond abrasive paste, to obtain the femoral ball head having a multilayer shell-core composite structure including alumina ceramic—interlayer of $ZrO_2(3Y_2O_3)$-80 wt. % $Al_2O_3$—core of $ZrO_2(3Y_2O_3)$-20 wt. % $Al_2O_3$, which has a smooth finished surface, and a proper dimensional coordination between the bore-hole 3 and the femoral component.

Third Embodiment

Figure 7:
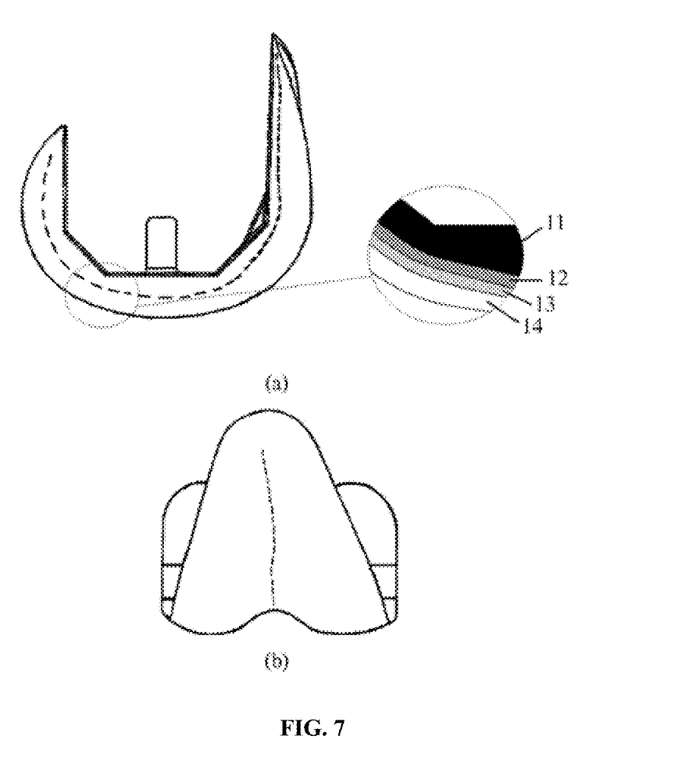
FIG. 7 schematically illustrates a cross-sectional view of a femoral condyle prosthesis (prosthetic knees) having a multilayer shell-core composite structure according to a third embodiment of the present disclosure, where the drawing (a) is a side-view, and the drawing (b) is a front-view.

Referring to FIG. 7, a femoral condyle prosthesis (one component of an artificial knee-joint) having a multilayer shell-core composite structure, includes a Ti6Al4V core layer 11, a transition layer 12 of Ti6Al4V-20 vol. % $Al_2O_3$, a transition layer 13 of Ti6Al4V-60 vol. % $Al_2O_3$, and a high-purity and superfine ceramic shell layer 14.

Referring to FIG. 6, a method for manufacturing a femoral condyle prosthesis having a multilayer shell-core composite structure in the third embodiment may include:

(1) preparing feedstocks for powder injection molding which include high-purity and superfine alumina powder, compound powder of Ti6Al4V-60 vol. % $Al_2O_3$, compound powder of Ti6Al4V-20 vol. % $Al_2O_3$, and Ti6Al4V powder. The high-purity and superfine alumina powder may have a purity greater than 99.9 wt %, have a particle size ranging from 0.5 μm to 5 μm. The Ti6Al4V powder may have a purity greater than 99.5 wt %, have a particle size ranging from 10 μm to 35 μm. In order to decrease sintering temperature and improve sintering performance, magnesium oxide (MgO) powder with a concentration of 0.1 wt. % may be added into the high-purity and superfine alumina powder as sintering aids. After preparation, the modified alumina powder, compound powder of Ti6Al4V-60 vol. % $Al_2O_3$, compound powder of Ti6Al4V-20 vol. % $Al_2O_3$, and Ti6Al4V powder are mixed with polyoxymethylene resin binder (89 wt. % polyformaldehyde, 5 wt. % high density polyethylene and 6 wt. % other binding assistant agent), respectively. The mixture is then mixed under a temperature of about 180° C. for about two and a half hours, so that a feedstock of a polyaldehydes system is obtained, which has a solid loading (solid content) greater than 60 vol. %.

(2) by using four sets of moulds, performing co-injection molding successively to obtain the Ti6Al4V core layer 11, the transition layer 12 of Ti6Al4V-20 wt. % $Al_2O_3$, the transition layer 13 of Ti6Al4V-80 wt. % $Al_2O_3$ and the high-purity and superfine alumina ceramic shell layer 14 of the femoral condyle prosthesis having a multilayer shell-core composite structure. Firstly, feedstocks including Ti6Al4V polyaldehydes are injected into a first mould to obtain the Ti6Al4V core layer 11 of the femoral condyle prosthesis. Then, by using the Ti6Al4V core layer 11 as an insert, a complex with the transition layer 12 of Ti6Al4V-20 wt. % $Al_2O_3$ covering the Ti6Al4V core layer 11 may be obtained through injection molding in a second mould. Then, by using the complex of the transition layer 12 of Ti6Al4V-20 wt. % $Al_2O_3$/the Ti6Al4V core layer 11 as an insert, a compound covered by the transition layer 13 of Ti6Al4V-80 wt. % $Al_2O_3$ may be obtained through injection molding in a third mould. Then, by using the complex of the transition layer 13 of Ti6Al4V-80 wt. % $Al_2O_3$/the transition layer 12 of Ti6Al4V-20 wt. % $Al_2O_3$/the Ti6Al4V core layer 11 as an insert, a green body of the femoral condyle prosthesis having a multilayer shell-core composite structure which is covered by the high-purity and superfine $Al_2O_3$ ceramic shell layer 14, may be obtained through injection molding in a fourth mould. The temperature of the injection may be in a range from about 170° C. to about 180° C., the pressure of the injection may be in a range from about 100 MPa to about 120 MPa, the dwell pressure may be in a range from about 70 MPa to about 85 MPa, and the cooling time may be in a range from about 3 minutes to about 4 minutes.

(3) if necessary, performing surface finishing on the alumina shell layer 14 and the Ti6Al4V core layer 11 of the green body of the femoral condyle prosthesis having a multilayer shell-core composite structure.

(4) performing catalytic debinding on the green body of the femoral condyle prosthesis having a multilayer shell-core composite structure in an atmosphere furnace with a temperature ranging from about 110° C. to about 120° C., where hydrogen nitrate is used as debinding catalyst, nitrogen is used as debinding carrier gas, and the catalytic debinding may last for about 5 hours.

(5) after being catalytic debound, sintering the green body of the femoral condyle prosthesis having a multilayer shell-core composite structure in a controlled atmosphere Hot Isostatic Pressing (HIP) furnace, where the sintering may be performed at a temperature of about 1420° C., a pressure of about 40 MPa, and the soaking time is about 1 hour, so that an alumina shell layer 4 which has a relative density greater than 99.5% and a hardness greater than HV1950, densified and toughed transition layers 12 and 13, and a Ti6Al4V core layer 11 which has a high fracture toughness and has a relative density greater than 99.0%, may be obtained.

(6) according to size requirements of the products, performing micro-machining on the alumina shell layer 14 of the sintering body of the femoral condyle prosthesis having a multilayer shell-core composite structure.

(7) then, polishing the alumina shell layer 14 by using SiC ultrafine powder and diamond abrasive paste, to obtain the femoral condyle prosthesis having a multilayer shell-core composite structure, which has a smooth finished surface.

Fourth Embodiment

Figure 8:
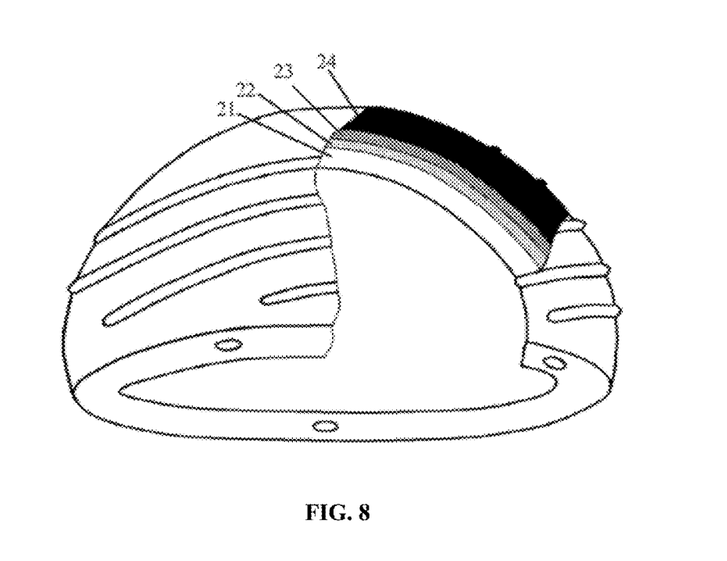
FIG. 8 schematically illustrates a cross-sectional view of an artificial acetabulum having a multilayer shell-core composite structure according to a fourth embodiment of the present disclosure.

Referring to FIG. 8, an acetabulum (one component of an artificial hip joint) having a multilayer shell-core composite structure, includes a high-purity and superfine $Al_2O_3$ ceramic core layer 21, a transition layer 22 of Ti6Al4V-60 vol. % $Al_2O_3$, a transition layer 23 of Ti6Al4V-20 vol. % $Al_2O_3$, and a Ti6Al4V shell layer 24.

Referring to FIG. 6, a method for manufacturing an acetabulum having a multilayer shell-core composite structure in the fourth embodiment may include:

(1) preparing feedstocks for powder injection molding which include high-purity and superfine alumina powder, compound powder of Ti6Al4V-60 vol. % $Al_2O_3$, compound powder of Ti6Al4V-20 vol. % $Al_2O_3$, and Ti6Al4V powder. The high-purity and superfine alumina powder may have a purity greater than 99.9 wt %, have a particle size ranging from 0.5 μm to 5 μm. The Ti6Al4V powder may have a purity greater than 99.5 wt %, have a particle size ranging from 10 μm to 35 μm. In order to decrease sintering temperature and improve sintering performance, magnesium oxide (MgO) powder with a concentration of 0.1 wt. % may be added into the high-purity and superfine alumina powder as sintering aids. After preparation, the modified alumina powder, compound powder of Ti6Al4V-60 vol. % $Al_2O_3$, compound powder of Ti6Al4V-20 vol. % $Al_2O_3$, and Ti6Al4V powder are mixed with polyoxymethylene resin binder (89 wt. % polyformaldehyde, 5 wt. % high density polyethylene and 6 wt. % other binding assistant agent), respectively. The mixture is then mixed under a temperature of about 180° C. for about two and a half hours, so that a polyaldehydes system is obtained, which has a solid loading (solid content) greater than 60 vol. %.

(2) by using four sets of moulds, performing co-injection molding successively to obtain the high-purity and superfine $Al_2O_3$ ceramic core layer 21, the transition layer 22 of Ti6Al4V-60 vol. % $Al_2O_3$, the transition layer 23 of Ti6Al4V-20 vol. % $Al_2O_3$ and the Ti6Al4V shell layer 24 of the acetabulum having a multilayer shell-core composite structure. Firstly, feedstocks including Ti6Al4V polyaldehydes are injected into a first mould to obtain the Ti6Al4V shell layer 24. Then, by using the Ti6Al4V shell layer 24 as an inserts, a complex with the transition layer 23 of Ti6Al4V-20 wt. % $Al_2O_3$ covering the Ti6Al4V shell layer 24 may be obtained through injection molding in a second mould. Then, by using the complex of the transition layer 23 of Ti6Al4V-20 wt. % $Al_2O_3$/the Ti6Al4V shell layer 24 as an inserts, a complex covered by the transition layer 22 of Ti6Al4V-80 wt. % $Al_2O_3$ may be obtained through injection molding in a third mould. Then, by using the complex of the transition layer 22 of Ti6Al4V-80 wt. % $Al_2O_3$/the transition layer 23 of Ti6Al4V-20 wt. % $Al_2O_3$/the Ti6Al4V shell layer 24 as an inserts, a green body of the acetabulum having a multilayer shell-core composite structure which is covered by the high-purity and superfine $Al_2O_3$ ceramic core layer 21, may be obtained through injection molding in a fourth mould. The temperature of the injection may be in a range from about 170° C. to about 180° C., the pressure of the injection may be in a range from about 100 MPa to about 120 MPa, the dwell pressure may be in a range from about 70 MPa to about 85 MPa, and the cooling time may be in a range from about 3 minutes to about 4 minutes.

(3) if necessary, performing surface finishing on the $Al_2O_3$ ceramic core layer 1 and the Ti6Al4V shell layer 24 of the green body of the acetabulum having a multilayer shell-core composite structure.

(4) performing catalytic debinding on the green body of the acetabulum having a multilayer shell-core composite structure in an atmosphere furnace with a temperature ranging from about 110° C. to about 120° C., where hydrogen nitrate is used as debinding catalyst, nitrogen is used as debinding carrier gas, and the catalytic debinding may last for about 5 hours.

(5) after being catalytic debound, sintering the green body of the acetabulum having a multilayer shell-core composite structure in a controlled atmosphere Hot Isostatic Pressing (HIP) furnace, where the sintering may be performed at a temperature of about 1420° C., a pressure of about 40 MPa, and the soaking time is about 1 hour, so that an alumina core layer 21 which has a relative density greater than 99.5% and a hardness greater than HV1950, transition layers 22 and 23 which are densified and toughed, and a Ti6Al4V shell layer 24 which has a high fracture toughness and has a relative density greater than 99.0%, may be obtained.

(6) according to size requirements of the products, performing micro-machining on a surface of the alumina core layer 21 of the sintering body of the acetabulum having a multilayer shell-core composite structure.

(7) then, polishing a surface of the alumina core layer 21 by using SiC ultrafine powder and diamond abrasive paste, to obtain the acetabulum having a multilayer shell-core composite structure, which has a smooth finished surface, and a proper dimensional coordination with a femoral ball head.

Fifth Embodiment

Figure 9:
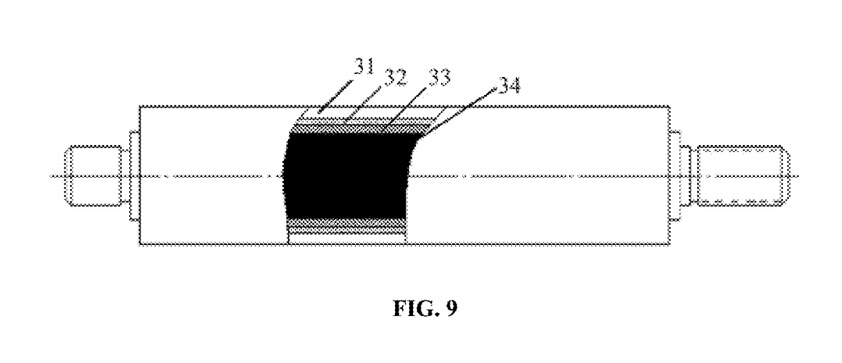
FIG. 9 schematically illustrates a cross-sectional view of a plunger having a multilayer shell-core composite structure according to a fifth embodiment of the present disclosure.

Referring to FIG. 9, a plunger having a multilayer shell-core composite structure, is composed of a $ZrO_2(Y+Ce)$ shell layer 31, a second transition layer 32 of 17-4PH stainless steel −60 vol. % $ZrO_2(Y+Ce)$, a first transition layer 33 of 17-4PH stainless steel −30 vol. % $ZrO_2(Y+Ce)$, and a 17-4PH stainless steel core spindle 34.

Referring to FIG. 6 in conjunction with FIG. 9, a method for manufacturing a ceramic plunger having a multilayer shell-core composite structure in the fifth embodiment may include:

(1) preparing feedstocks for powder injection molding which include $ZrO_2$(Y+Ce) powder, compound powder of 17-4PH stainless steel −60 vol. % $ZrO_2$(Y+Ce), compound powder of 17-4PH stainless steel −30 vol. % $ZrO_2$(Y+Ce), and 17-4PH stainless steel powder. The $ZrO_2$ powder may have a purity greater than 98.5 wt %, have a particle size ranging from 0.2 μm to 0.5 μm. The 17-4PH stainless steel powder may have a purity greater than 98.8 wt %, have a particle size ranging from 5 μm to 25 μm. In order to ensure performance, 1.5% mol $Y_2O_3$ powder and 4% mol $CeO_2$ powder may be added into the $ZrO_2$ powder as stabilizing additive, to obtain partially stabilized $ZrO_2$(Y+Ce)powder. After preparation, the modified $ZrO_2$(Y+Ce) powder, compound powder of 17-4PH stainless steel −60 vol. % $ZrO_2$ ((Y+Ce), compound powder of 17-4PH stainless steel −30 vol. % $ZrO_2$(Y+Ce), and 17-4PH stainless steel powder are mixed with polyoxymethylene resin binder (89 wt. % polyformaldehyde, 5 wt. % high density polyethylene and 6 wt. % other binding assistant agent), respectively. The mixture is then mixed under a temperature of about 180° C. for about two and a half hours, so that a polyaldehydes system is obtained, which has a solid loading (solid content) greater than 55 vol. %.

(2) by using four sets of moulds, performing co-injection molding successively to obtain the $ZrO_2$(Y+Ce) shell layer 31, the second transition layer 32 of 17-4PH stainless steel −60 vol. % $ZrO_2$(Y+Ce), the first transition layer 33 of 17-4PH stainless steel −30 vol. % $ZrO_2$(Y+Ce), and the 17-4PH stainless steel core spindle 34 of the ceramic plunger having a multilayer shell-core composite structure. Firstly, feedstocks including 17-4PH stainless steel polyaldehydes are injected into a chamber 61a in a first mould to obtain the 17-4PH stainless steel core spindle 34 of the ceramic plunger. Then, by using the stainless steel core spindle 34 as a first insertion, a first complex with the first transition layer 33 of 17-4PH stainless steel −30 vol. % $ZrO_2$(Y+Ce) covering the stainless steel core spindle 34 may be obtained through injection molding in a first space between the first insertion and a second mould. Then, by using the first complex of the first transition layer 33 of 17-4PH stainless steel −30 vol. % $ZrO_2$(Y+Ce)/the stainless steel core spindle 34 as a second insertion, a second complex covered by the second transition layer 32 of 17-4PH stainless steel −60 vol. % $ZrO_2$(Y+Ce) may be obtained through injection molding in a second space between the second insertion and a third mould. At last, by using the second complex of the second transition layer 32 of 17-4PH stainless steel −60 vol. % $ZrO_2$(Y+Ce)/the first transition layer 33 of 17-4PH stainless steel −30 vol. % $ZrO_2$(Y+Ce)/the stainless steel core spindle 34 as a third insertion, a green body of the ceramic plunger having a multilayer shell-core composite structure which is covered by the superfine $ZrO_2$(Y+Ce) ceramic shell layer 31, may be obtained through injection molding in a third space between the third insertion and a fourth mould. The temperature of the injection may be in a range from about 170° C. to about 180° C., the pressure of the injection may be in a range from about 100 MPa to about 120 MPa, the dwell pressure may be in a range from about 70 MPa to about 85 MPa, and the cooling time may be in a range from about 3 minutes to about 4 minutes.

(3) if necessary, performing surface finishing on the $ZrO_2$(Y+Ce) shell layer 31 and the 17-4PH stainless steel core spindle 34 of the green body of the ceramic plunger having a multilayer shell-core composite structure.

(4) performing catalytic debinding on the green body of the ceramic plunger having a multilayer shell-core composite structure in an atmosphere furnace with a temperature ranging from about 110° C. to about 120° C., where hydrogen nitrate is used as debinding catalyst, nitrogen is used as debinding carrier gas, and the catalytic debinding may last for about 5 hours.

(5) after being catalytic debound, sintering the green body of the ceramic plunger having a multilayer shell-core composite structure in a controlled atmosphere Hot Isostatic Pressing (HIP) furnace, where the sintering may be performed at a temperature of about 1350° C., a pressure of about 35 MPa, and the soaking time is about 1 hour, so that a $ZrO_2$ shell layer 31 which has a relative density greater than 98.8% and a hardness greater than HV1500, transition layers 32 and 33 which are densified and toughed, and a 17-4PH stainless steel core spindle 4, may be obtained.

(6) according to size requirements of the products, performing micro-machining on a surface of the $ZrO_2$(Y+Ce) shell layer 31, and performing machining on both ends of the 17-4PH stainless steel core spindle 34.

(7) finally, polishing a surface of the $ZrO_2$(Y+Ce) shell layer 31 by using SiC ultrafine powder and diamond abrasive paste, to obtain the ceramic plunger having a multilayer shell-core composite structure, which has a smooth finished surface, and a proper dimensional coordination with a mantle of the ceramic plunger.

Sixth Embodiment

Figure 10:
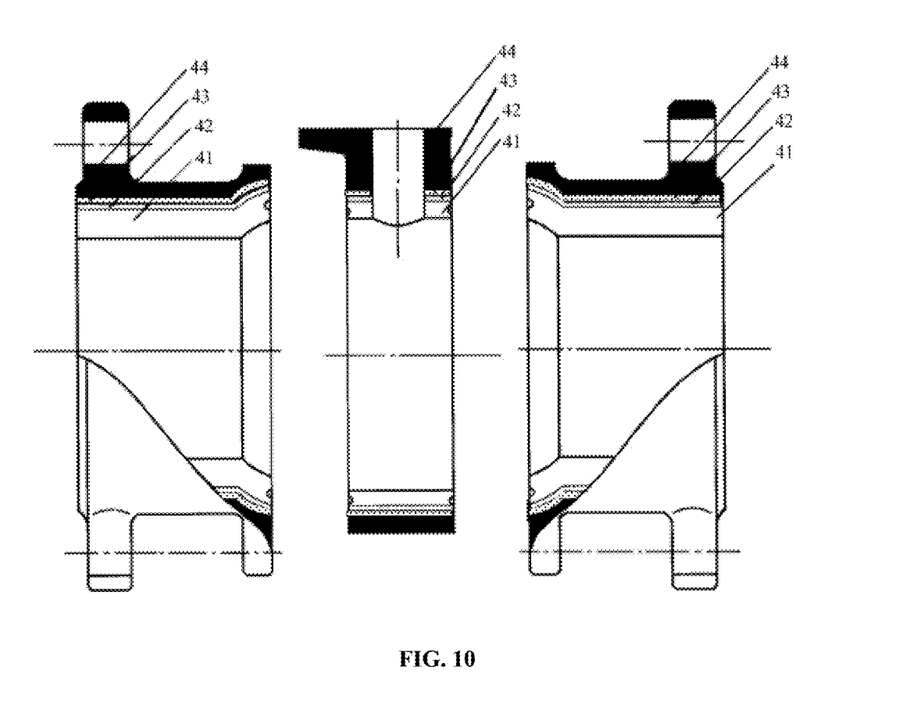
FIG. 10 schematically illustrates a cross-sectional view of a ball valve body having a multilayer shell-core composite structure according to a sixth embodiment of the present disclosure, where the drawings on both sides show a bonnet respectively, and the drawing in the middle shows a valve body.

Referring to FIG. 10, a fully padded ceramic ball valve body (including one valve body and two bonnets) having a multilayer shell-core composite structure, is composed of a $ZrO_2$(Y+Ce) valve liner 41, a transition layer 42 of 17-4PH stainless steel −60 vol. % $ZrO_2$(Y+Ce), a transition layer 43 of 17-4PH stainless steel −30 vol. % $ZrO_2$(Y+Ce), and a 17-4PH stainless steel valve shell 44.

Referring to FIG. 6, a method for manufacturing a fully padded ceramic ball valve body having a multilayer shell-core composite structure in the sixth embodiment may include:

(1) preparing feedstocks for powder injection molding which include $ZrO_2$(Y+Ce) powder, compound powder of 17-4PH stainless steel −60 vol. % $ZrO_2$(Y+Ce), compound powder of 17-4PH stainless steel −30 vol. % $ZrO_2$(Y+Ce), and 17-4PH stainless steel powder. The $ZrO_2$ powder may have a purity greater than 98.5 wt %, have a particle size ranging from 0.2 μm to 1.5 μm. The 17-4PH stainless steel powder may have a purity greater than 98.8 wt %, have a particle size ranging from 5 μm to 35 μm. In order to improve performance, 1.5% mol $Y_2O_3$ powder and 4% mol $CeO_2$ powder may be added into the $ZrO_2$ powder as stabilizing additive, to obtain partially stabilized $ZrO_2$(Y+Ce)powder. After preparation, the modified $ZrO_2$(Y+Ce) powder, compound powder of 17-4PH stainless steel −60 vol. % $ZrO_2$(Y+Ce), compound powder of 17-4PH stainless steel −30 vol. % $ZrO_2$(Y+Ce), and 17-4PH stainless steel powder are mixed with polyoxymethylene resin binder (89 wt. % polyformaldehyde, 5 wt. % high density polyethylene and 6 wt. % other binding assistant agent), respectively. The mixture is then mixed under a temperature of about 180° C. for about two and a half hours, so that a polyaldehydes system is obtained, which has a solid loading (solid content) greater than 55 vol. %.

(2) by using four sets of moulds, performing co-injection molding successively to obtain the $ZrO_2(Y+Ce)$ valve liner 41, the transition layer 42 of 17-4PH stainless steel −60 vol. % $ZrO_2(Y+Ce)$, the transition layer 43 of 17-4PH stainless steel −30 vol. % $ZrO_2(Y+Ce)$, and the 17-4PH stainless steel valve shell 44 of the fully padded ceramic ball valve body having a multilayer shell-core composite structure. Firstly, feedstocks including 17-4PH stainless steel polyaldehydes are injected into a first mould to obtain the 17-4PH stainless steel valve shell 44. Then, by using the stainless steel valve shell 44 as an inserts, a complex with the transition layer 43 of 17-4PH stainless steel −30 vol. % $ZrO_2(Y+Ce)$ covering the stainless steel valve shell 44 may be obtained through injection molding in a second mould. Then, by using the complex of the transition layer 43 of 17-4PH stainless steel −30 vol. % $ZrO_2(Y+Ce)$/the stainless steel valve shell 44 as an inserts, a complex covered by the transition layer 42 of 17-4PH stainless steel −60 vol. % $ZrO_2(Y+Ce)$ may be obtained through injection molding in a third mould. At last, by using the complex of the transition layer 42 of 17-4PH stainless steel −60 vol. % $ZrO_2(Y+Ce)$/the transition layer 43 of 17-4PH stainless steel −30 vol. % $ZrO_2(Y+Ce)$/the stainless steel valve shell 44 as an inserts, a green body of the fully padded ceramic ball valve body having a multilayer shell-core composite structure which is covered by the superfine $ZrO_2(Y+Ce)$ valve liner 41, may be obtained through injection molding in a fourth mould. The temperature of the injection may be in a range from about 170° C. to about 180° C., the pressure of the injection may be in a range from about 100 MPa to about 120 MPa, the dwell pressure may be in a range from about 70 MPa to about 85 MPa, and the cooling time may be in a range from about 3 minutes to about 4 minutes.

(3) if necessary, performing surface finishing on the $ZrO_2(Y+Ce)$ valve liner 41 and the 17-4PH stainless steel valve shell 44 of the green body of the fully padded ceramic ball valve body having a multilayer shell-core composite structure.

(4) performing catalytic debinding on the green body of the fully padded ceramic ball valve body having a multilayer shell-core composite structure in an atmosphere furnace with a temperature ranging from about 110° C. to about 120° C., where hydrogen nitrate is used as debinding catalyst, nitrogen is used as debinding carrier gas, and the catalytic debinding may last for about 5 hours.

(5) after being catalytic debound, sintering the green body of the fully padded ceramic ball valve body having a multilayer shell-core composite structure in a controlled atmosphere Hot Isostatic Pressing (HIP) furnace, where the sintering may be performed at a temperature of about 1350° C., a pressure of about 35 MPa, and the soaking time is about 1 hour, so that a $ZrO_2(Y+Ce)$ valve liner 41 which has a relative density greater than 98.8% and a hardness greater than HV1450, densified and toughed transition layers 42 and 43, and a 17-4PH stainless steel valve shell 44, may be obtained.

(6) according to size requirements of the products, performing micro-machining on a surface of the $ZrO_2(Y+Ce)$ valve liner 41, and if necessary, performing machining on the 17-4PH stainless valve shell 44.

(7) finally, polishing a surface of the $ZrO_2(Y+Ce)$ valve liner 41 by using SiC ultrafine powder and diamond abrasive paste, especially a round surface of the $ZrO_2(Y+Ce)$ valve liner 41 of two bonnets, so as to obtain the fully padded ceramic ball valve body having a multilayer shell-core composite structure, which has a smooth finished surface, and a proper dimensional coordination with a valve spool of the ceramic ball valve.

Although the present disclosure has been disclosed above with reference to preferred embodiments thereof, it should be understood that the disclosure is presented by way of example only, and not limitation. Those skilled in the art can modify and vary the embodiments without departing from the spirit and scope of the present disclosure.

What is claimed is:

1. A method for manufacturing an acetabulum having a multilayer shell-core composite structure, comprising:
    preparing feedstocks of a shell layer, at least one transition layer and a core layer respectively;
    performing a powder injection molding with the feedstocks, to obtain a green body of the acetabulum comprising the shell layer, the at least one transition layer and the core layer;
    performing debinding on the green body of the acetabulum; and
    sintering the green body of the acetabulum after being debound, to obtain the acetabulum;
    wherein preparing a feedstock of each of the shell layer, the at least one transition layer and the core layer comprises: mixing a main powder of the each layer, a binder and an additive comprising a surface active agent and a plasticizer to obtain a mixture, where the main powder of the core layer is made of a powdered ceramic material, the main powder of the shell layer is made of a metal powder material or a powdered toughened ceramic material, and the main powder of the at least one transition layer comprises at least one mixed powder formed by mixing the main powder of the shell layer with the main powder of the core layer at a ratio,
    wherein the binder comprises polyoxymethylene resin;
    wherein preparing the feedstock of each of the shell layer, the at least one transition layer and the core layer further comprises:
    heating the mixture at a temperature greater than a melting point of the polyoxymethylene resin for a time period, so as to obtain a feedstock of polyaldehydes system having a solid content greater than 60 vol. %.

2. The method according to claim 1, wherein the powder injection molding with the feedstocks is performed at temperatures higher than a melting point of the polyoxymethylene resin and comprises a cooling duration.

3. The method according to claim 1, wherein the polyoxymethylene resin binder comprises 89 wt. % polyformaldehyde, 5 wt. % high density polyethylene and 6 wt. % other binding assistant agent.

4. The method according to claim 1, wherein the powdered ceramic material is selected from a group consisting of alumina, zirconia, titanium carbide, chromium carbide, silicon carbide, boron carbide, zirconium carbide, tantalum carbide, tungsten carbide, titanium nitride, chromium nitride, boron nitride, silicon nitride, zirconium nitride and tantalum nitride, or combinations thereof; the powdered toughened ceramic material is selected from a group consisting of cermet, $ZrO_2$ toughened ceramic, whisker toughened ceramic and fiber toughened ceramic, or combinations thereof and the metal powder material is selected from a group consisting of niobium, zirconium, titanium, molybdenum, tantalum, cobalt, chromium, vanadium, aluminum and iron, or combinations thereof.

5. The method according to claim 1, wherein the main powder of the at least one transition layer comprises a plurality of mixed powders formed by mixing the main powder of the shell layer with the main powder of the core layer at different ratios to form multiple sub-layers of the at least one transition layer; and the multiple sub-layers are formed between the shell layer and the core layer, where the main powder of the shell layer takes up a main proportion in the main powders of some of the multiple sub-layers closer to the shell layer than to the core layer, and the main powder of the core layer takes up a main proportion in the main powders of the multiple sub-layers closer to the core layer than to the shell layer.

6. The method according to claim 5, wherein a feedstock of each of the multiple sub-layers of the at least one transition layer is prepared respectively, and green bodies of the multiple sub-layers are formed using the powder injection molding process respectively.

7. The method according to claim 1, wherein the method further comprises: performing surface finishing on the green body of the acetabulum prior to debinding.

8. The method according to claim 1, wherein each of the shell layer, the at least one transition layer and the core layer has a thickness ranging from about 0.1 mm to about 20 mm, and a relative density of more than 97%.

9. The method according to claim 1, wherein the main powder of the core layer is alumina powder and the main powder of the shell layer is Ti6A14V powder; and wherein the at least one transition layer comprises a first sub-layer closer to the shell layer and a second sub-layer closer to the core layer, the main powder of the first sub-layer is compound powder of Ti6A14V-20 vol. % $Al_2O_3$, and the main powder of the second sub-layer is compound powder of Ti6A14V-60 vol. % $Al_2O_3$.

10. The method according to claim 9, wherein, the powder injection molding is performed at a temperature ranging from about 170° C. to about 180° C., a pressure ranging from about 100 MPa to about 120 MPa, a dwell pressure ranging from about 70 MPa to about 85 MPa, and a cooling duration ranging from about 3 minutes to about 4 minutes.

11. The method according to claim 9, wherein the debinding on the green body comprises a catalytic debinding process, which is performed in an atmosphere furnace with a temperature ranging from about 110° C. to about 120° C., with hydrogen nitrate used as a debinding catalyst and nitrogen used as a debinding carrier gas, and with a debinding duration of 5 hours.

12. The method according to claim 9, wherein the green body is sintered in a controlled atmosphere Hot Isostatic Pressing (HIP) furnace, with a sintering temperature of about 1420° C., a pressure of about 40 MPa, and a soaking time of about 1 hour.

13. The method according to claim 9, wherein the alumina powder has a purity greater than 99.9 wt %, and a particle size ranging from 0.5 μm to 5 μm; and the Ti6A14V powder has a purity greater than 99.5 wt %, and a particle size ranging from 10 μm to 35 μm.

14. The method according to claim 9, wherein the feedstocks further comprise magnesium oxide powder added to the alumina powder as a sintering aid.

15. The method according to claim 1, wherein the debinding process comprises catalytic debinding, heating debinding, dissolution extraction debinding, supercritical fluid extraction (SFE) debinding or siphon debinding.

16. The method according to claim 1, wherein a Vickers-Hardness of a surface of the core layer is greater than 1950, and/or a fracture toughness of the shell layer is greater than 8 MPa·m$^{1/2}$.

* * * * *